United States Patent [19]

Occelli et al.

[11] Patent Number: 5,306,715
[45] Date of Patent: Apr. 26, 1994

[54] RIFAPENTINE HYDROHALIDES

[75] Inventors: Emilio Occelli, Parabiago; Marino Nebuloni, Rho; Bruno Cavalleri, Milan, all of Italy

[73] Assignee: Gruppo Lepetit SpA, Milan, Italy

[21] Appl. No.: 635,172

[22] PCT Filed: Jun. 21, 1989

[86] PCT No.: PCT/EP89/00694
§ 371 Date: Jan. 8, 1991
§ 102(e) Date: Aug. 1, 1991

[87] PCT Pub. No.: WO90/00553
PCT Pub. Date: Jan. 25, 1990

[30] Foreign Application Priority Data

Jul. 13, 1988 [GB] United Kingdom ............... 8816620

[51] Int. Cl.$^5$ ................... A61K 31/395; C07D 498/08

[52] U.S. Cl. .................. 514/183; 514/255; 540/458

[58] Field of Search ............... 540/458; 514/183, 255

[56] References Cited

U.S. PATENT DOCUMENTS

| 3,342,810 | 9/1967 | Maggi et al. | 540/458 |
|---|---|---|---|
| 4,002,752 | 1/1977 | Cricchio et al. | 540/458 |

FOREIGN PATENT DOCUMENTS 2608218 9/1976 Fed. Rep. of Germany ...... 540/458

OTHER PUBLICATIONS

Derwent Abstract of FR2309556.

Primary Examiner—Robert T. Bond
Attorney, Agent, or Firm—J. Michael Dixon

[57] ABSTRACT

A solid rifapentine hydrohalide useful for anti-bacterial purposes.

14 Claims, 10 Drawing Sheets

FIG. 1

DSC HEATING CURVES OF RIFAPENTINE HYDROCHLORIDE
a) FORM I (EXAMPLE 1.1); b) FORM II (EXAMPLE 1.2);
c) AMORPHOUS (EXAMPLE 1.3)

FIG.2a

IR SPECTRA OF RIFAPENTINE HYDROCHLORIDE IN NUJOL MULL: a) FORM I (EXAMPLE 1.1); b) FORM II (EXAMPLE 1.2)

FIG.2c

IR SPECTRA OF RIFAPENTINE HYDROCHLORIDE IN NUJOL MULL AND IN CDCL3 SOLUTION: C) AMORPHOUS (EXAMPLE 1.5); d) IN CDCL3 SOLUTION (EXAMPLE 1.3)

FIG.2d

IR SPECTRA OF RIFAPENTINE HYDROCHLORIDE IN NUJOL
MULL AND IN CDCL3 SOLUTION: C) AMORPHOUS (EXAMPLE 1.5);
d) IN CDCL3 SOLUTION (EXAMPLE 1.3)

FIG. 3

DSC HEATING CURVES OF RIFAPENTINE HYDROBROMIDE a) FORM I; b) FORM II; c) AMORPHOUS

FIG.4a

IR SPECTRA OF RIFAPENTINE HYDROBROMIDE IN NUJOL MULL: a) FORM I; b) FORM II

FIG.4b

IR SPECTRA OF RIFAPENTINE HYDROBROMIDE IN NUJOL MULL: a) FORM I; b) FORM II

FIG. 4d

IR SPECTRA OF RIFAPENTINE HYDROBROMIDE IN NUJOL MULL AND IN CDCl$_3$ SOLUTION: c) AMORPHOUS; d) IN CDCl$_3$ SOLUTION

RIFAPENTINE HYDROHALIDES

The object of this invention is an hydrohalic acid addition salt of rifapentine of the formula wherein X is chlorine or bromine.

A further particular object of this invention is an hydrohalic acid addition salt of rifapentine according to the above formula in the solid form.

Rifapentine is an antibacterial compound showing a long lasting action which is disclosed in U.S. Pat. No. 4,002,752 and particularly useful for the treatment of acute pulmonary infections. See also, M. Tsukamura et al., Kekkaku (Tuberculosis, Japan), 1986, 61/12, (633–639); P.E. Varlado et al., antimicrobial Agents Chemother, (USA), 1985, 27/4, (615–618); Yi Lu et al., Chin. J. antib. (China), 1987, 12/5, (341–344).

The process of manufacture of rifapentine disclosed in U.S. Pat. No. 4,002,752 yields a solid rifapentine free base in several different forms, having different solubility and bioavailability characteristics. The applicant have so far obtained six different forms of solid rifapentine (one crystalline modification, five solvates—two of which with ethanol, one with methanol, one with ethyl acetate and one with toluene—and the amorphous phase) by slightly changing the operation conditions, e.g. the type of solvent or the temperature of crystallization. Most frequently, when operating according to the general methods and solvents described in U.S. Pat. No. 4,002,752 in industrial or pilot scale preparations, a mixture of two or more of said solid forms is obtained which results in a product of inconstant physical and biological characteristics.

Moreover, it has been observed that some of said forms are relatively instable during storage or under the manipulations necessary for the manufacture of the final dosage units (e.g. capsules, tablets, film-coated tablets, sugar-coated tablets, suspensions and the like) and therefore it is very difficult to maintain the biological characteristics of the dosage forms of the antibiotic substance at a constant level of performance and quality to assure a reliable therapeutical effect. A further disadvantage of the presence of said relatively instable forms is that, in most cases, their modification during storage or under formulation manipulations promotes the transformation into the amorphous phase which is the solid form of rifapentine free base showing less favorable biological characteristics.

Therefore, it is desirable to provide rifapentine in a solid form displaying good and constant biological effects coupled with good stability of its physico-chemical characteristics.

According to the present invention it has been found that the new acid addition salts of rifapentine represented in formula I are solving such problems. Acid addition salts of rifapentine with strong mineral acids, in particular with hydrohalic acids, are not known in the prior art and, moreover, although several hydrazones of 3-formlyrifamycin SV with 1-aminopiperazines variously substituted in the position 4 are reported (see for instance: U.S. Pat. Nos. 3,342,810, 3,796,798, 4,002,754 and W. Germany Patent Application 2816274), no example of strong mineral acid addition salts thereof is disclosed.

The hydrohalides of rifapentine of formula I can be obtained by common procedures which consist in contacting rifapentine free base with a hydrohalic acid of the formula HX wherein X is chlorine or bromine.

The solid rifapentine hydrohalides are preferably obtained by contacting rifapentine free base with an excess of diluted aqueous hydrohalic acid of the formula HX as above defined at a temperature between 0° and 40° C., preferably at the room temperature, for a period of time sufficient for the completion of the salification process. The solid obtained is separated from the reaction mixture by filtration or centrifugation and, after washing with cool water, is recristallized from an organic solvent or a mixture thereof or is precipitated from an organic solution by addition of a non-solvent. The product obtained from crystallization is a stable monohydrohalide of rifapentine which, depending on the solvent system used for its crystallization, shows a crystalline polymorph form or an amorphous form.

Two crystalline forms have been identified both showing high stability during storage or with handling for the manufacture of the solid dosage unit forms.

Each crystalline form and the amorphous state have been characterized by thermal parameters, by IR spectroscopy, by X-Ray powder diffraction and by thermomicroscopy.

The crystalline modification of rifapentine mono hydrochloride showing melting point at 192° C. has been identified as Form I while the crystalline modification showing a broad endotherm in the temperature range 180°–220° C. has been identified as Form II.

Form I has been obtained by crystallization from methanol, while Form II has been obtained by crystallization from acetone or ethanol:chloroform mixtures. A characteristic of both forms is that they contain not less than 2% by weight of water (generally from 2.0% to 3.0%) in their crystalline lattice and that, once the water is completely removed by heating at about 120° C., the original amounts of water is taken again completely in a short time. Both forms do not show any modification when stored at room temperature for six months. Transformation of Form I into the amorphous form requires a prolonged grinding in a mortar while the conversion of Form II into the amorphous form occurs in a shorter time.

The amorphous form can be obtained also by crystallization from ethyl acetate or by precipitation from chloroform by addition of ethyl ether. The amorphous form is physically stable on grinding and shows high affinity for water since it takes up about 4% of water from the surrounding with grinding. The amorphous form melts in the temperature interval of 185°–190° C.

The hydrobromide of rifapentine shows two crystalline forms which have been identified as Form I (melting point 198° C.) and Form II (showing a broad endotherm between 210° C. and 220° C.). These forms are obtained by crystallizing the hydrobromide under the same conditions as described above for the hydrochloride. An amorphous form is also obtained by precipitation from a solution by addition of an appropriate non-solvent as described above for the hydrochloride. The amorphous form of the hydrobromide melts with decomposition at 175° C.

The microbiological activity of the rifapentine hydrohalides is essentially the same as that of rifapentine free base. The same conclusion can be drawn with regard to the bioavailability characteristics.

Representative bioavailability test are carried out in rats administered by oral route with a water-methocel suspension of rifapentine hydrochloride (Form I) in comparison with a water-methocel suspension of a sample of rifapentine free base (obtained according to the process described in U.S. Pat. No. 4,002,752 and crystallized from ethanol; the resulting product is crystalline rifapentine free base) which is currently used for manufacturing dosage unit forms employed in clinical trials. The results of the tests show that both products have substantially similar pharmacokinetic profile.

A further object of this invention is to provide pharmaceutical dosage forms containing the hydrohalide salts of rifapentine. The pharmaceutical dosage forms includes oral solid dosage units such as capsules, tablets, troches, film-coated tablets, sugar-coated tablets, hard gelatin capsules, soft elastic capsules, and the like. These forms can contain the rifapentine hydrohalides powder admixed with the usual inert excipients such as diluents, binders, disintegrants, and lubricants. These additives are essentially the same which can be used in the formulations of similar antibiotics, e.g., rifampicin.

Other pharmaceuticals dosage forms which can be used for either oral administration or external applications include solutions, syrups, suspensions, emulsions and the like. Also in these cases the methods and ingredients usually employed for the formulation of similar antibiotics, e.g. rifampicin, can be successfully utilized. Pharmaceutical dosage forms for parenteral administration are also comprised in this particular aspect of the invention. These pharmaceutical dosage forms include preparations suitable for subcutaneous, intramuscular and intravenous administration which, optionally, can be formulated as dry solid products ready to be combined with the appropriate vehicle just prior to the use.

The rifapentine hydrohalides may be also administered as medicated applications through the skin or various body orifices. Accordingly, they are applied to the skin or inserted into body orifices in liquid, semisolid or solid forms. This implies using pharmaceutical dosage forms like aerosol, ointments suppositories, and drug delivery systems.

The manufacture of the pharmaceutical dosage forms containing rifapentine hydrohalide can be carried out by commonly known procedures; see for instant: "Remington's Pharmaceutical Sciences, 17 Edition, (1985) Mack Publishing Co., East, Pa. 18042.

The above mentioned dosage forms show good stability characteristics, in particular the crystalline form of the rifapentine hydrohalides employed in solid dosage forms or suspensions remain substantially unchanged after storage at room temperature for six months.

EXAMPLES

Example 1

Preparation of Rifapentine Hydrochloride

A suspension of rifapentine (2 g) in 40 ml of 1N HCl is stirred for 90 minutes at room temperature, then the solid is collected by filtration and washed three times with 10 ml of cool water. After drying under vacuum at 40° C., 1.9 g of rifapentine monohydrochloride is obtained, which is recrystallized from a selected series of solvents.

1.1) Crystallization from methanol: Form I

The compound is dissolved in the minimal amount of boiling methanol. On standing at room temperature, a crystalline compound separates which is filtered off and washed with cold methanol and dried under vacuum.

1.2) Crystallization from acetone: Form II

The compound is treated with acetone in the same manner as described for methanol under paragraph 1.1 above.

1.3) Crystallization from ethyl acetate: Amorphous Form.

The compound is treated with ethyl acetate in the same manner as described for methanol under paragraph 1.1 above.

1.4) Crystallization from ethanol/chloroform: Form II

The compound (1 g) is suspended in boiling ethanol (25ml) and chloroform is added until a solution is obtained. The solution is concentrated to a small volume (10 ml). By standing a solid separates which is filtered off and washed with a little amount of ethanol.

1.5) Precipitation from chloroform/ethyl ether: Amorphous Form

To a hot solution of the compound (1 g) in chloroform (10 ml) ethyl ether is added until the separation of solid material occurs. After standing the solid is collected by filtration and washed with a little amount of ethyl ether.

1.6) The elemental composition of each of the above samples is determined using C, H, N elemental analyzer apparatus (C. Erba) before and after drying the samples at 150° C. in inert atmosphere, and for Cl, by titration in non-aqueous solvent after combustion into flask (Schoeniger method). The results correspond to the theoretical data within the experimental error. The content of water in the samples before drying at 150° C. is ranging between 2.0 to 3.0 per cent by weight.

1.7) Solid state characterization

Form I appears as anisotropic crystals with a not well defined habit.

Form II appears as anisotropic crystals with an aggregate-geminate habit.

The amorphous phase appears as isotropic powder without birefringence. Crystalline habits and phase transitions are observed with a crystallographic microscope and a Kofler hot stage microscope (HSM).

Figure 1:
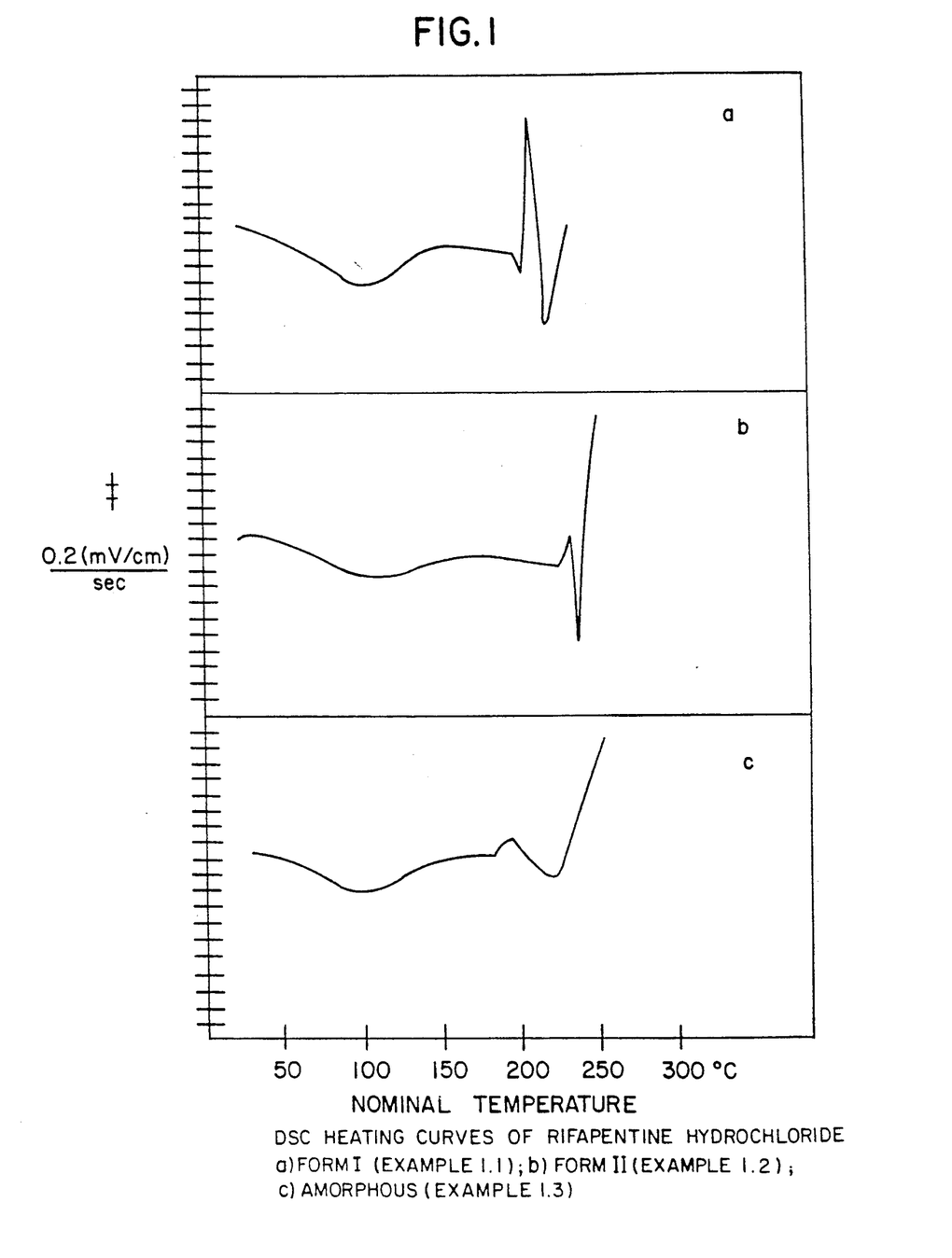
FIG. 1 depicts the DSC heating curves of rifapentine hydrochloride.
Figure 2A:
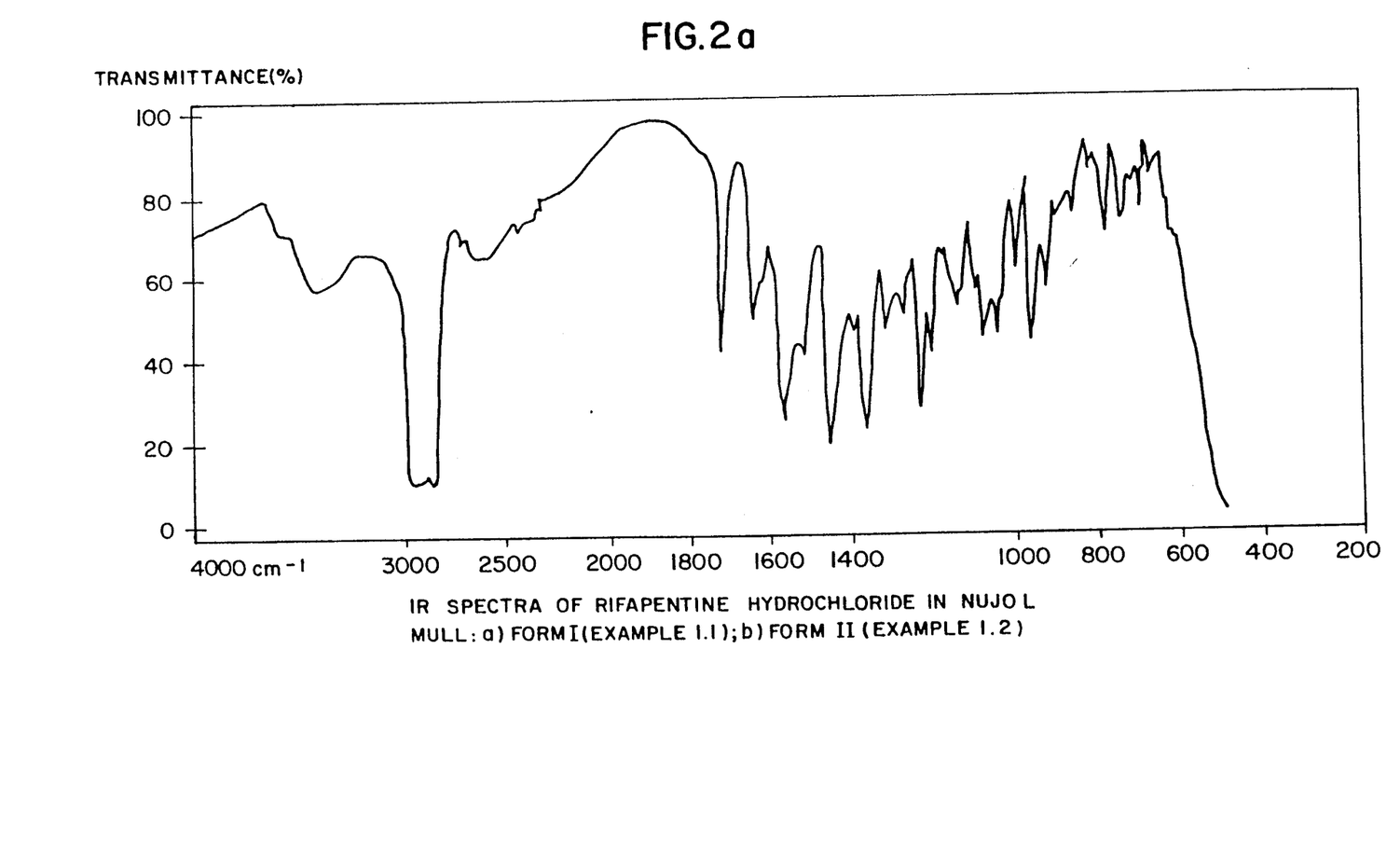
FIG. 2a–d depicts the DSC heating curves of rifapentine hydrochloride.
Figure 2B:
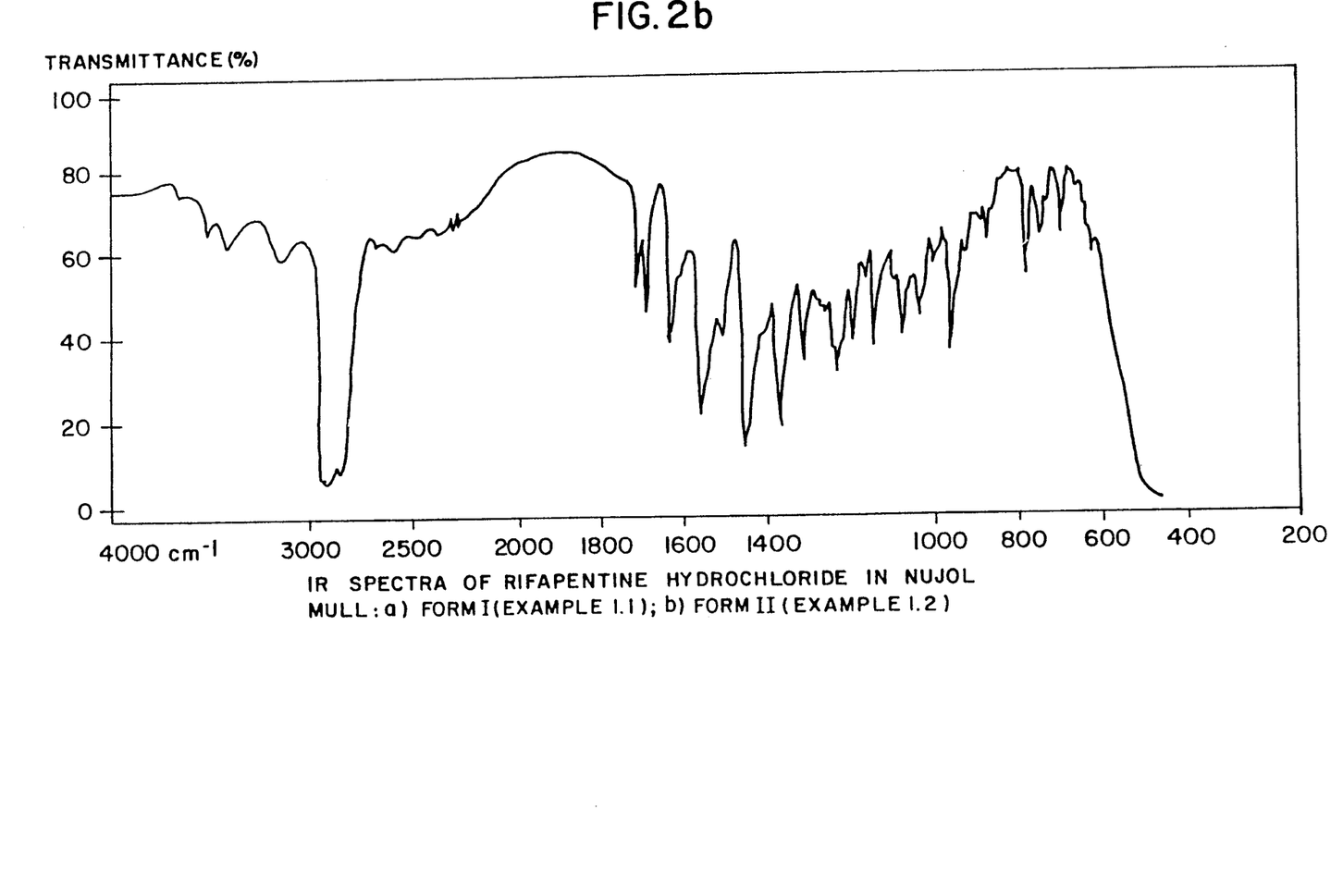
Figure 2C:
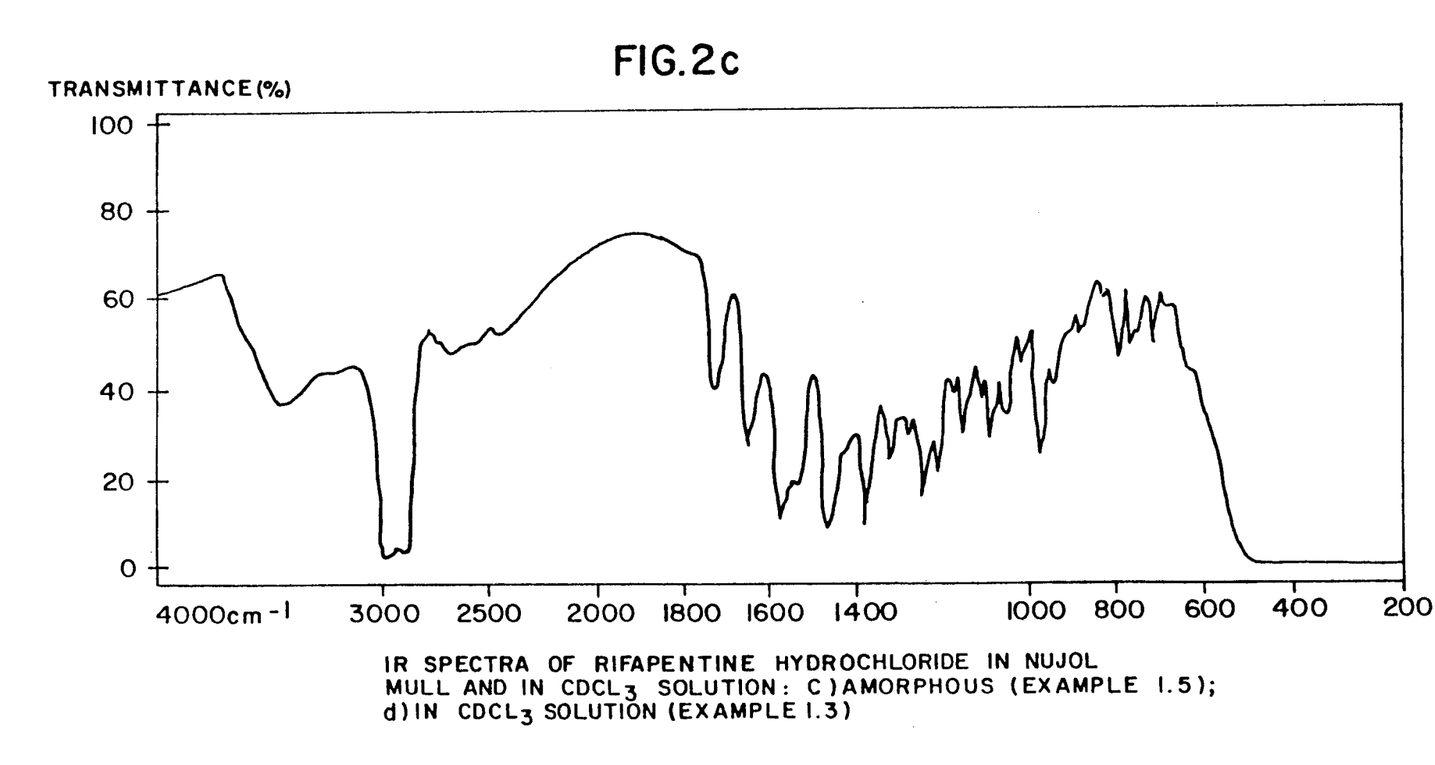
Figure 2D:
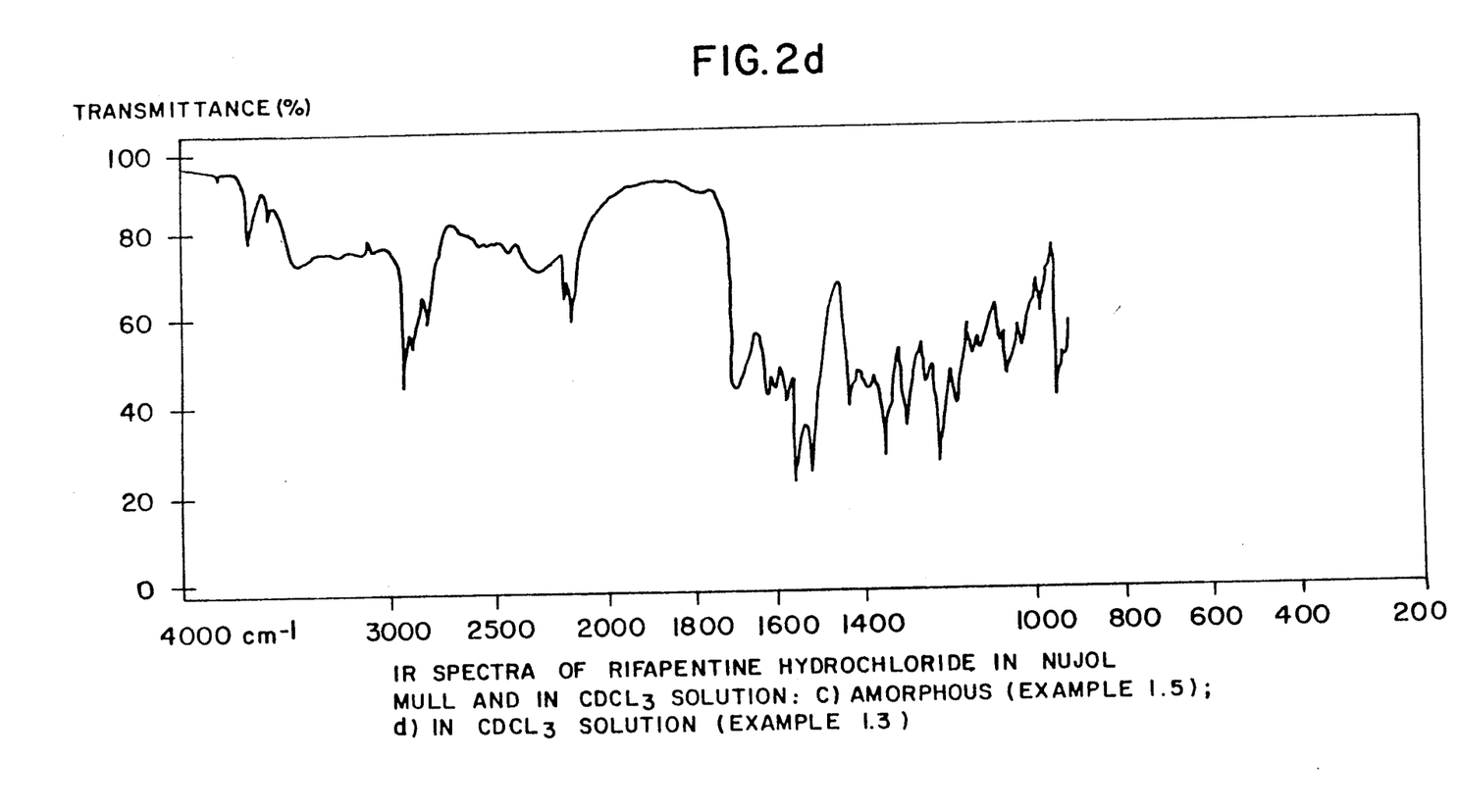

1.8) Thermal analysis (DSC-TG) is obtained with a Mettler TA 2000 or a Du Pont 900 thermoanalyzer and with a thermobalance. The working conditions are: gas flow: $N_2 = 25$ ml/min, scan speed: 10°/min, weight of sample: about 4 mg. TABLE I reports the thermal parameters, while FIGS. 1a, 1b and 1c show the DSC heating curves of the three solid forms.

Form I shows an endothermic peak at 192° C. (due to melting) immediately followed by decomposition (exothermic and endothermic peaks) which prevents the heat of melting to be reliably determined. At 40°–140° C. a desolvation endotherm, due to imbibition water, occurs.

Form II shows a broad endotherm in the temperature range 180°–220° C. followed by decomposition (exothermic and endothermic peaks). In the range of 20°–140° C. a weight loss due to imbibition water occurs.

The amorphous form shows an endotherm between 25°–150° C. with about 3% of weight loss. At about 185°–190° C. a baseline shift occurs, due to the melting, followed by decomposition of the compound.

1.9) Infrared spectra (IR) are recorded with a Perkin Elmer mod. 580 spectrophotometer in nujol mull and in $CDCl_3$ solution. See FIGS. 2a, 2b, 2c, 2d and TABLE II.

1.10) X-Ray powder diffraction patterns of Form I and Form II, obtained with Philips (PW 1010/77, 1049/01, 4025/10) instrument, radiation $CuK_{alpha}$, are reported in TABLES III and IV.

Example 2

Preparation of Rifapentine Hydrobromide

A suspension of rifapentine (1 g) in 20 ml of 1N HBr is stirred for 90 minutes at room temperature, then the solid is collected by filtration and washed three times with 5 ml of cool water. After drying under vacuum at 40° C., 1.1 g of rifapentine monohydrobromide is obtained, which is rerystallized from a selected series of solvents.

2.1) Crystallization from methanol: Form I

The compound is prepared in the same manner as for the corresponding hydrochloride (see Example 1.1).

2.2) Crystallization from acetone: Form II

The compound is prepared on the same manner as for the corresponding hydrochloride (see Example 1.2)

2.3) Precipitation from chloroform/ethyl ether: Amorphous Form

To a hot solution of the compound (1 g) in chloroform (7 ml) ethyl ether is added until the separation of solid material occurs. After standing, the solid is collected by filtration and washed with a little amount of ethyl ether.

2.4) The elemental composition of each of the above samples is determined using C, H, N elemental analyzer apparatus (C. Erba) before and after drying the samples at 150° C., and for Br, by titration in non-aqueous solvent after combustion into flask (Schoeninger method).

The results correspond to the theoretical data within the experimental error.

Figure 3:
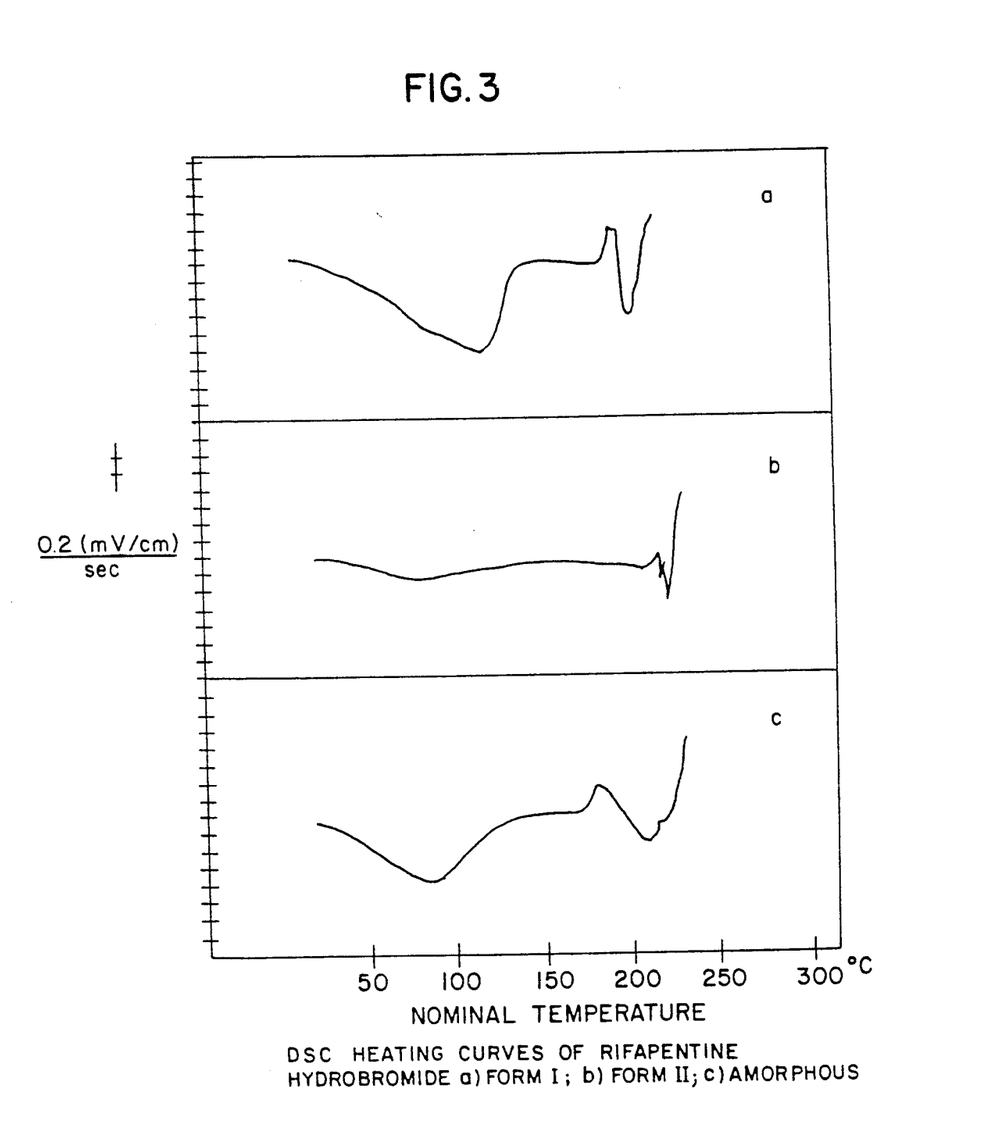
FIG. 3 depicts the heating curves of rifapentine hydrobromide.
Figure 4A:
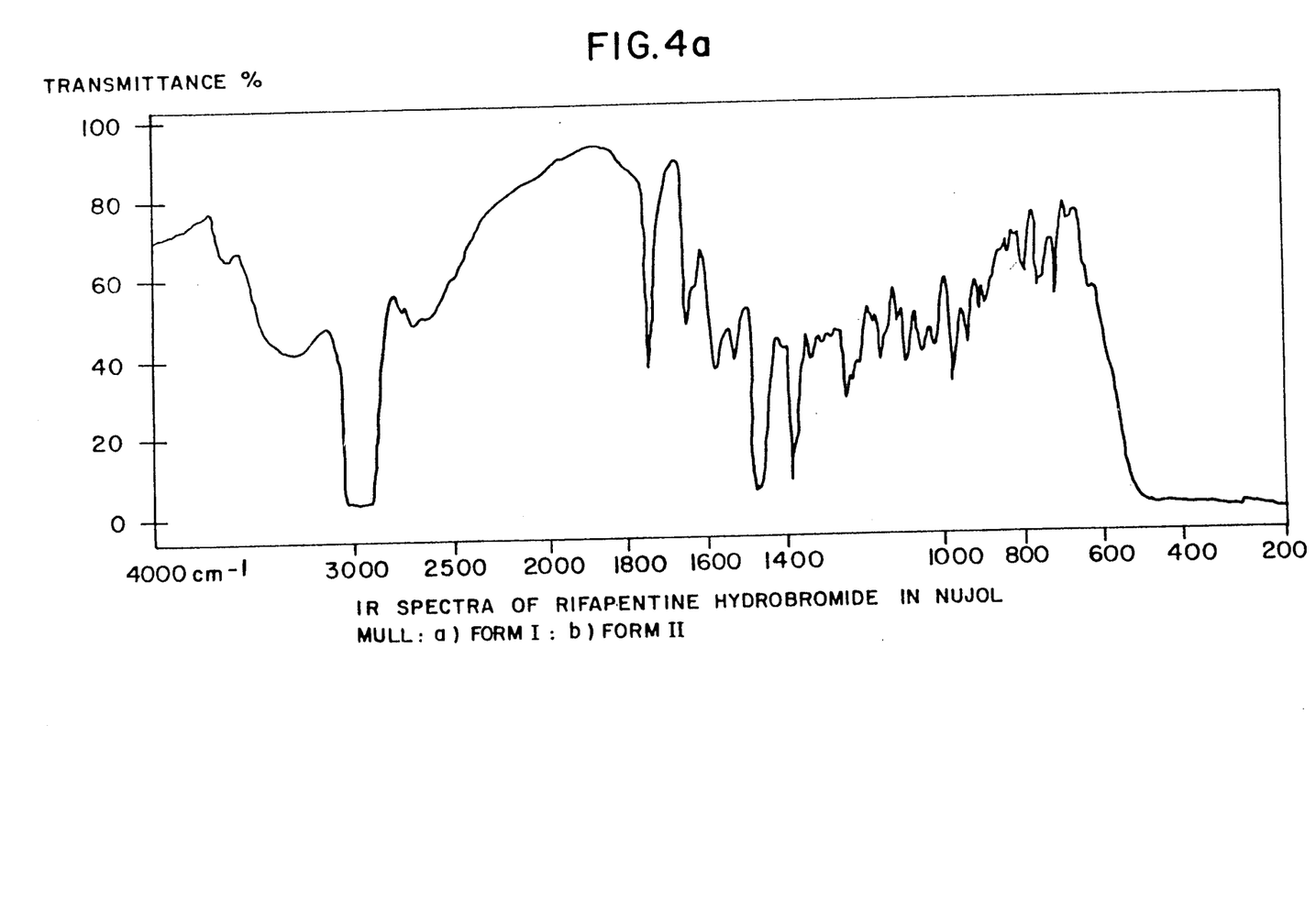
FIG. 4a–d depicts the IR spectra of rifapentine hydrobromide.
Figure 4B:
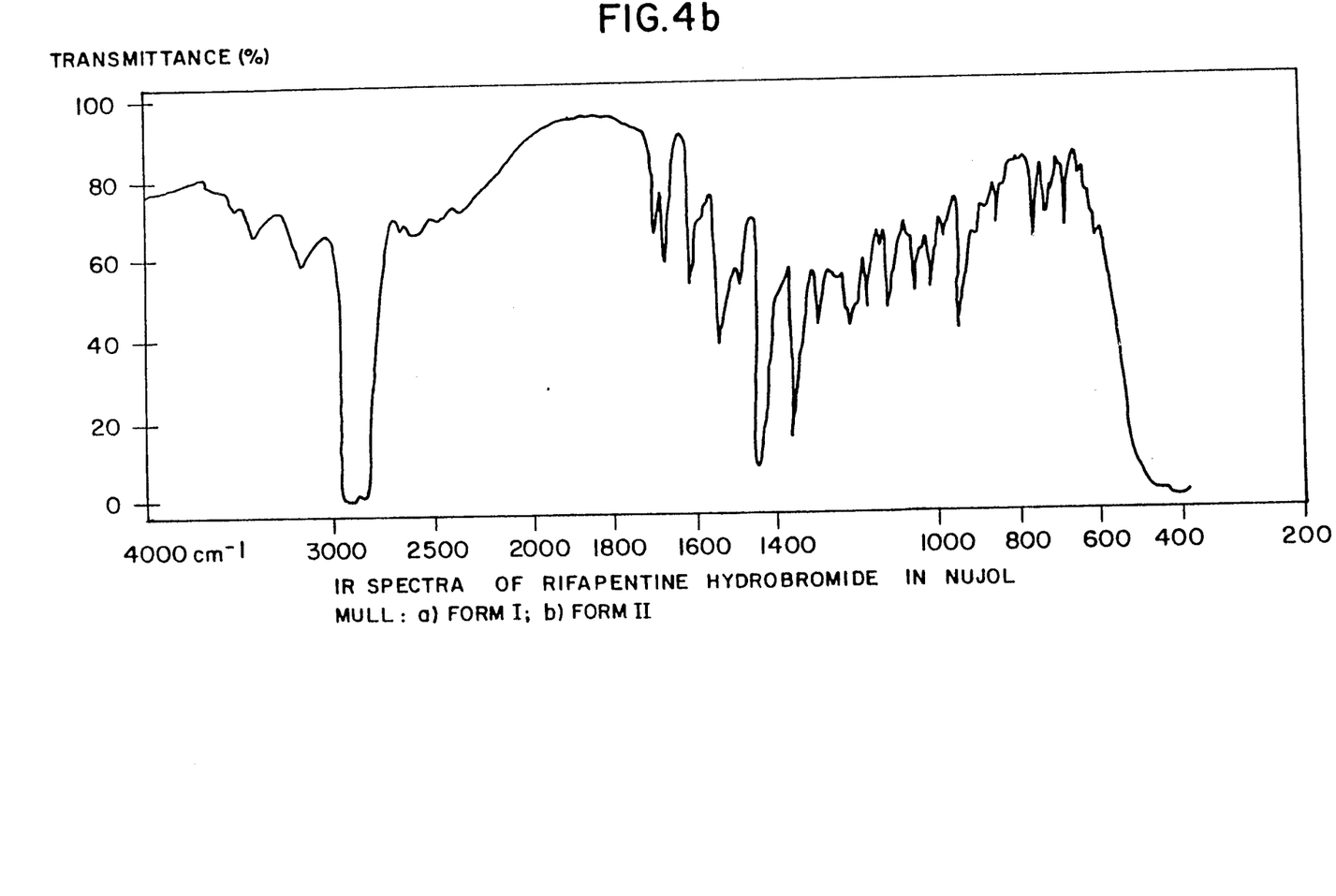
Figure 4C:
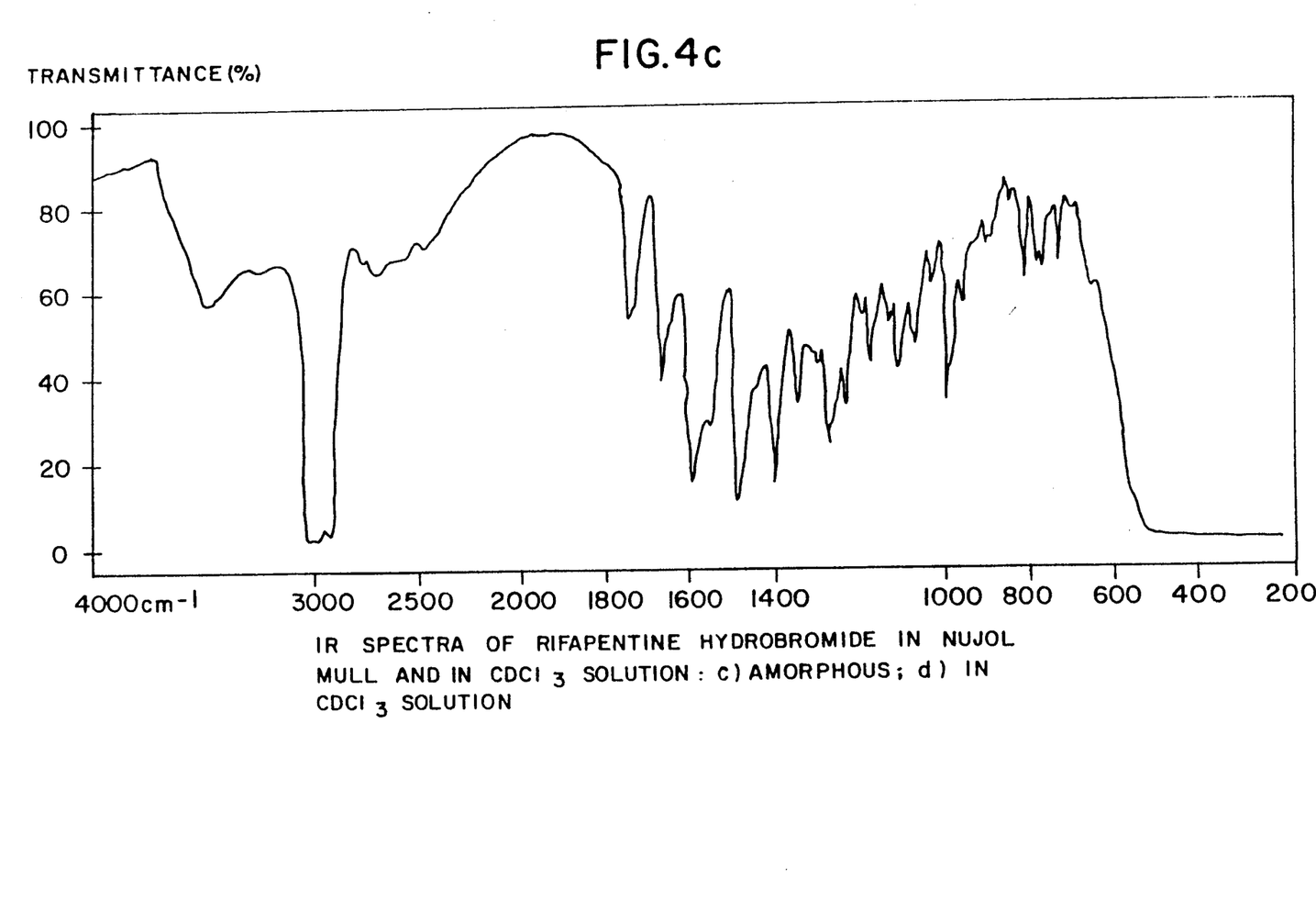
Figure 4D:
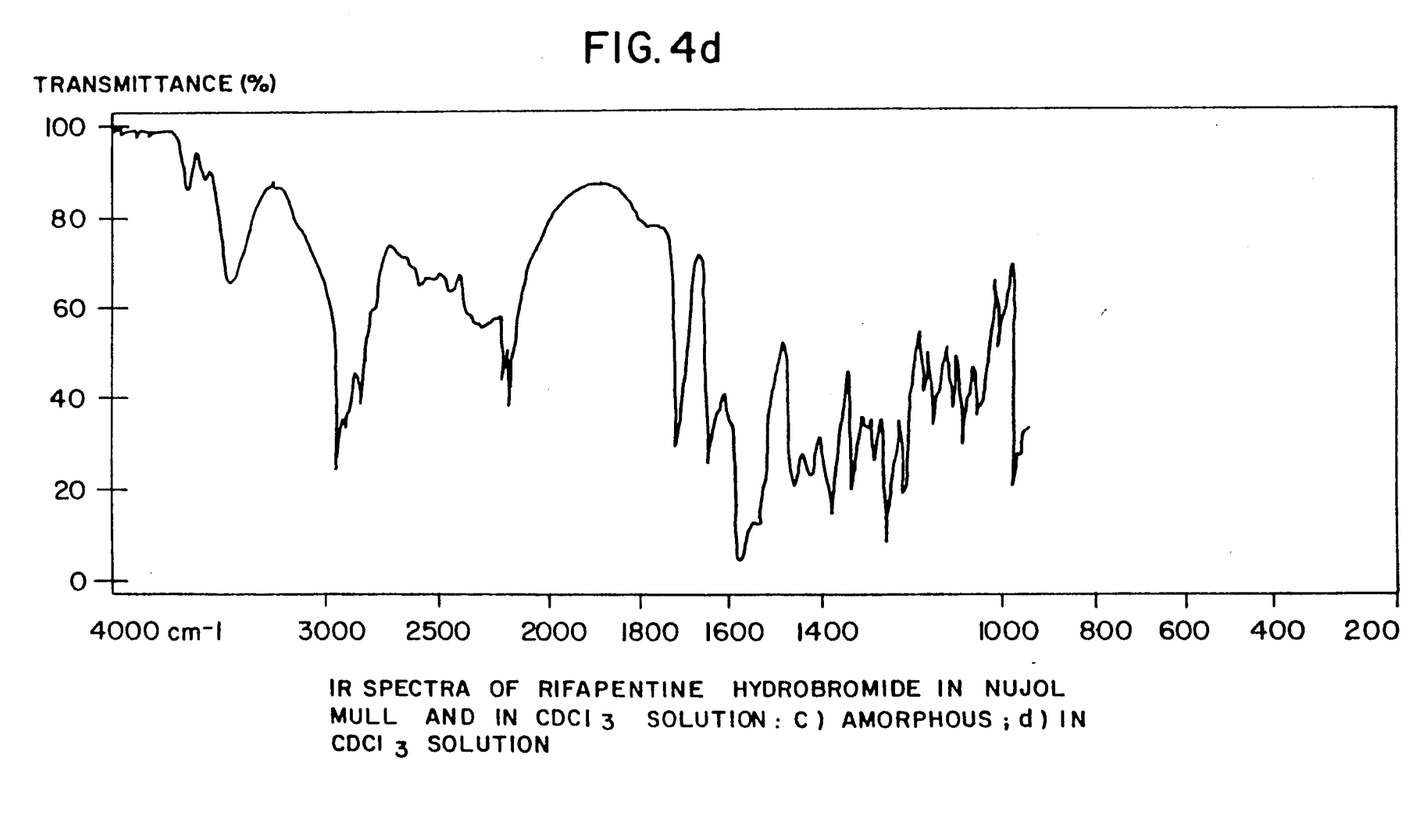

2.5) Thermal analysis (DSC-TG) is obtained with a Mettler TA 2000 or a Du Pont 990 thermoanalyzer and with a thermobalance. The working conditions are: gas flow: $N_2 = 25$ ml/min, scan speed: 10° C./min, weight of sample: about 4 mg. TABLE V reports the thermal parameters, while FIGS. 3a, 3b and 3c show the DSC heating curves of the three solid forms.

2.6) Infrared spectra (IR) are recorded with a Perkin Elmer Mod. 580 l spectrophotometer in nujol mull and in $CDCl_3$ solution. See FIGS. 4a, 4b, 4c, 4d.

Example 3

3.1) A sugar coated tablet containing rifapentine hydrohalide as the active ingredient has the following composition:

| | |
|---|---|
| Rifapentine hydrohalide (crystalline Form I or II or amorphous form) (as free base) | 150 mg |
| Sodium lauryl sulfate | 0.5 mg |
| Microgranulated cellulose | 15 mg |
| Lactose | 20 mg |
| Arabic gum | 10 mg |
| $MgCO_3$ | 4 mg |
| $TiO_2$ | 6 mg |
| Talc | 30 mg |
| Kaolin | 5 mg |
| Calcium Stearate | 2 mg |
| Sucrose | 115 mg |
| Carboxymethyl cellulose (sodium) | 11 mg |
| Polivynyl pyrrolidone K30 | 1.5 mg |
| Aluminium lacquer E 127 | 0.5 mg |
| Colloidal silicon | 0.5 mg |

3.2) A capsule containing rifapentine hydrochloride as the active ingredient has the following composition:

| | |
|---|---|
| Rifapentine hydrochloride (crystalline Form I or II or amorphous form) (as free base) | 150 mg |
| Mais starch | 23 mg |
| Calcium stearate | 2 mg |

3.3) A syrup suspension containing rifapentine hydrochloride as the active ingredient has the following composition:

| | |
|---|---|
| Rifapentine hydrochloride (Form I or Form II or amorphous form) (as free base) | 1 g |
| Ascorbic acid | 100 mg |
| Agar-agar | 170 mg |
| Saccharin | 50 mg |
| Sucrose | 20 mg |
| Methyl p. hydroxybenzoate | 120 mg |
| Propyl p. hydroxybenzoate | 30 mg |
| Polysorbate monoleate | 10 mg |
| Fruit essence | 0.4 ml |
| Purified water | as to 100 ml |

3.4) A kit for reconstitution of an aqueous solution for use in i.v. applications, cavities lavages or topical applications has the following composition: Active ingredient vial:

| | |
|---|---|
| Rifapentine hydrochloride (Form I or II or amorphous form) (as free base) | 300 mg |
| Solvent vial: | |
| Sodium hydroxide 1 N | to pH 9.5 |
| Purified water | to 5 ml |

In the above examples of pharmaceutical dosage forms rifapentine hydrochloride may be substituted with rifapentine hydrobromide (form I or II or amorphous form).

TABLE I

Thermal parameters of rifapentine hydrochloride

| Form | M.p. or transition temp. °C. | Weight loss %(**) |
| --- | --- | --- |
| I (example 1.1) | 192°* | 2.5 |
| II (example 1.2) | 180–220°* | 2.7 |
| amorphous (example 1.3) | 185–190°* | 3.0 |

\* = transition followed by rapid decomposition
\*\* = imbibition water (40–140° C.)

TABLE II

Assignment of the main functional infrared bands (cm$^{-1}$) of rifapentine hydrochloride

| | Form | ansa $\nu OH$ | furanone $\nu C-O$ | acetil $\nu C-O$ | amide $\nu C-O$ | acetyl $\nu C-O-C$ |
| --- | --- | --- | --- | --- | --- | --- |
| I | (example 1.1) | 3500–3300 | 1645 | 1730 | 1625 | 1245 |
| II | (example 1.2) | 3540, 3440, 3180 | 1740 | 1715 | 1645 | 1250 |
| amorphous | (example 1.5) | 3440, 3300 | 1645 | 1720 | 1625 | 1250 |
| CDCl$_3$ sol. | (example 1.3) | 3460 | 1645 | 1720 | 1620 | 1250 |

TABLE III

X-ray diffraction pattern of rifapentine hydrochloride - Form I (example 1.1) according to ASTM
Wave-lengths: ALPHA 1 = 1.54051 Angström
ALPHA 2 = 1.54433
ALPHA - MEAN = 1.54178

| No. | Theta degree | D Angström | Intensity |
| --- | --- | --- | --- |
| The five strongest reflections are: | | | |
| 2 | 3.35 | 13.19 | 100 |
| 5 | 4.9 | 9.02 | 72 |
| 8 | 6.65 | 6.65 | 59 |
| 3 | 3.95 | 11.19 | 58 |
| 9 | 7 | 6.32 | 48 |
| Diffraction Pattern: | | | |
| 1 | 2.9 | 15.24 | 8 |
| 2 | 3.35 | 13.19 | 100 |
| 3 | 3.95 | 11.19 | 58 |
| 4 | 4.4 | 10.05 | 12 |
| 5 | 4.9 | 9.02 | 72 |
| 6 | 5.5 | 8.04 | 8 |
| 7 | 6 | 7.37 | 24 |
| 8 | 6.65 | 6.65 | 59 |
| 9 | 7 | 6.32 | 48 |
| 10 | 7.3 | 6.06 | 13 |
| 11 | 7.65 | 5.79 | 30 |
| 12 | 7.9 | 5.6 | 32 |
| 13 | 8.15 | 5.43 | 14 |
| 14 | 8.75 | 5.06 | 17 |
| 15 | 9.3 | 4.77 | 33 |
| 16 | 9.5 | 4.67 | 19 |
| 17 | 9.85 | 4.5 | 12 |
| 18 | 10.6 | 4.19 | 30 |
| 19 | 11 | 4.04 | 24 |
| 20 | 11.25 | 3.95 | 15 |
| 21 | 11.7 | 3.8 | 14 |
| 22 | 12 | 3.7 | 24 |
| 23 | 12.6 | 3.53 | 9 |
| 24 | 13.45 | 3.31 | 13 |

TABLE IV

X-ray diffraction patter of rifapentine hydrochloride - Form II (example 1.2) according to ASTM
Wave-lenghts: ALPHA 1 = 1.54051 Angström
ALPHA 2 = 1.54433
ALPHA - MEAN = 1.54178

| No. | Theta degree | D Angström | Intensity |
| --- | --- | --- | --- |
| The five strongest reflections are: | | | |
| 12 | 6.9 | 6.41 | 100 |
| 3 | 3.7 | 11.94 | 52 |
| 17 | 9.1 | 4.87 | 40 |
| 22 | 11.2 | 3.96 | 35 |
| 5 | 4.5 | 9.82 | 31 |
| Diffraction pattern: | | | |
| 1 | 2.7 | 16.36 | 10 |
| 2 | 2.9 | 15.24 | 6 |
| 3 | 3.7 | 11.94 | 52 |
| 4 | 3.9 | 11.33 | 19 |
| 5 | 4.5 | 9.82 | 31 |
| 6 | 4.8 | 9.21 | 7 |
| 7 | 4.95 | 8.93 | 7 |
| 8 | 5.2 | 8.5 | 13 |
| 9 | 5.65 | 7.83 | 27 |
| 10 | 5.85 | 7.56 | 12 |
| 11 | 6.25 | 7.08 | 26 |
| 12 | 6.9 | 6.41 | 100 |
| 13 | 7.4 | 5.98 | 6 |
| 14 | 7.6 | 5.82 | 6 |
| 15 | 8 | 5.54 | 25 |
| 16 | 8.3 | 5.34 | 14 |
| 17 | 9.1 | 4.87 | 40 |
| 18 | 9.5 | 4.67 | 14 |
| 19 | 9.9 | 4.48 | 12 |
| 20 | 10.2 | 4.35 | 18 |
| 21 | 10.45 | 4.25 | 13 |
| 22 | 11.2 | 3.96 | 35 |
| 23 | 11.7 | 3.8 | 11 |
| 24 | 12 | 3.7 | 17 |
| 25 | 12.5 | 3.56 | 12 |
| 26 | 13.2 | 3.37 | 11 |
| 27 | 13.85 | 3.22 | 6 |
| 28 | 14.35 | 3.11 | 4 |
| 29 | 14.65 | 3.04 | 4 |
| 30 | 14.85 | 3 | 3 |

TABLE V

Thermal parameters of rifapentine hydrobromide

| Form | M.p. or transition temperature. °C. | Weight loss % (interval. °C.) |
| --- | --- | --- |
| I | 198* | 7.5 (25–155) |
| II | 210–220* | 3.5 (30–140) |
| amorphous | 175* | 5.2 (30–130) |

\* = transition followed by rapid decomposition

We claim:
1. A solid acid addition salt of rifapentine of the formula wherein X is chlorine or bromine in the solid form.

2. An acid addition salt of claim 1 wherein X is chlorine, which is a crystalline solid melting at 192° C.

3. An acid addition salt of claim 1 wherein X is chlorine, which is a crystalline solid showing a broad entotherm at 180°–220° C. followed by decomposition.

4. An acid addition salt of claim 1 wherein X is chlorine, which is an amorphous solid melting in the interval 185°–190° C.

5. An acid addition salt of claim 1 wherein X is bromine, which is a crystalline solid melting at 198° C.

6. An acid addition salt of claim 1 wherein X is bromine, which is a crystalline solid showing a broad endotherm between 210° and 220° C.

7. An acid addition salt of claim 1 wherein X is bromine, which is an amorphous solid melting with decomposition at 175° C.

8. A process for the manufacture of a solid rifapentine acid addition salt of formula I wherein X is chlorine or bromine in the solid form which comprises contacting rifapentine free base with an acid of the formula HX wherein X is bromine or chlorine; and collecting said solid.

9. A process as in claim 8 wherein rifapentine free base is contacted with an excess of a diluted aqueous acid of the formula HX at a temperature between 0° and 40° C., preferably at the room temperature, for a period of time sufficient for the completion of the salification process and recovering the solid which separates from the reaction mixture.

10. A process as in claim 9 further characterized in that the product recovered is recrystallized from an organic solvent or a mixture thereof or is precipitated from an organic solution by addition of a non-solvent.

11. A process as in claim 10 wherein the crystallization solvent is selected from methanol, acetone, ethyl acetate or a mixture ethanol/chloroform.

12. A process as in claim 10 when the product recovered is precipitated from a chloroform solution by addition of ethyl ether.

13. A pharmaceutical antibacterial dosage form comprising rifapentine hydrochloride or rifapentine hydrobromide as the active ingredient present in an antibacterially effective amount in admixture with inert excipients.

14. A method for the treatment of bacterial infections comprising administering to a patient in need thereof an antibacterially effective amount of a dosage form according to claim 13.

* * * * *